United States Patent [19]

Zoeller et al.

US005144070A

[11] Patent Number: 5,144,070
[45] Date of Patent: Sep. 1, 1992

[54] PROCESS FOR THE PREPARATION OF α-IODOCARBONYL COMPOUNDS

[75] Inventors: Joseph R. Zoeller; Michael R. Cushman, both of Kingsport, Tenn.; Regina M. Moncier, Bristol, Va.

[73] Assignee: Eastman Kodak Company, Rochester, N.Y.

[21] Appl. No.: 400,421

[22] Filed: Aug. 30, 1989

[51] Int. Cl.$^5$ ..................... C07C 27/00; C07C 51/00
[52] U.S. Cl. .................................... 562/887; 568/319; 568/323; 568/354; 568/386; 568/397
[58] Field of Search ............... 562/887, 888; 570/141, 570/142, 201; 568/319, 323, 354, 386, 397

[56] References Cited
PUBLICATIONS

Burger, Alfred: Medicinal Chemistry, 2nd Edition, p. 36, 1964.

Primary Examiner—Marianne M. Cintins
Assistant Examiner—Margaret Argo
Attorney, Agent, or Firm—J. Frederick Thomsen; William P. Heath, Jr.

[57] ABSTRACT

Disclosed is a process for the preparation of α-iodocarbonyl compounds such as α-iodocarboxylic acid anhydrides and α-iodoketones by the reaction of a carboxylic anhydride with molecular iodine. Hydrolysis of the α-iodocarboxylic acid anhydrides gives the corresponding α-iodocarboxylic acids.

10 Claims, No Drawings

PROCESS FOR THE PREPARATION OF α-IODOCARBONYL COMPOUNDS

This invention pertains to a process for the preparation of α-iodocarbonyl compounds such as α-iodocarboxylic acids, anhydrides and ketones. More specifically, this invention pertains to the addition of molecular iodine to carboxylic anhydrides to obtain α-iodocarboxylic acids, anhydrides and ketones.

The literature contains numerous references to uses of α-iodocarboxylic acids and derivatives thereof, primarily in the biological arts. For example, the tumor inhibiting properties of iodoacetic acids and esters thereof are described by M. S. Rheins, J. A. Filppi, and V. S. Moore, Cancer Res., 35, 1514 (1975) and F. S. Liotti and P. Locci, Boll. Ist. Serioter. Milan., 65, 61 (1986). The prophylactic effect of α-iodoacetic acid esters in the prevention of parasitic infections by *Schistosomiasis Japonica* is described by F. Bai, Z. Leng, H. Ying, R. Wang, S. Zou, and X. Gu, Yaoxue Xuebao, 16, 621 (1981). There are several other industrial uses for α-iodocarboxylic acids and esters. For example, the use of α-iodocarboxylic acids and their esters, especially iodoacetic and α-iodopropanoic acids, in the manufacture of antibacterial plywood is described in Japanese Patent 82-92,076. The use of iodoacetic acid as an image stabilizer in silver halide photographic processing is disclosed in Japanese Patents 74-81,033 and 86-112,145. The α-iodocarboxylic acids also are useful chemical intermediates for the preparation of a wide variety of α-substituted carboxylic acids, for example, by the reaction thereof with various nucleophiles.

The use of iodoacetone as a catalyst for the chlorination of chloroacetone to produce 1,3-dichloroacetone is disclosed in British Patent 2,028,796. Its use as a bactericide in the production of sugar from sugar beets is described in German Offen. 2,258,886 and French Patent 2,163,470.

Those skilled in the art are aware that iodine generally will not iodinate organic substances by hydrogen extraction because the reaction of iodine and an organic substance to generate hydrogen iodide and an iodinated organic compound is thermodynamically disfavorable. Thus, halogenation of carboxylic acids with iodine has been rare and, for the most part, the synthesis of iodocarboxylic acids has been limited to exchanging iodide for either chlorine or bromine in preformed halogenated materials. See, for example, J. B. Conant and W. R. Kirner, J. Am. Chem. Soc., 46, 232 (1924); J. B. Conant and R. E. Hussey, J. Am. Chem. Soc., 47, 476 (1925); and J. B. Conant, W. R. Kirner, and R. E. Hussey, J. Am. Chem. Soc., 47, 488 (1925).

Successful methods using molecular iodine have been devised, although each entails some method of circumventing the thermodynamic problems associated with the formation of hydrogen iodide. These methods include the reaction of the carboxylic acid dianions (generated using lithium N-isopropylcyclohexylamide) with iodine [M. W. Rathke and A. Lindert, Tet. Lett., 3995 (1971)], the generation of α-iodoacyl chlorides from the reaction of acyl chlorides with iodine in thionyl chloride [D. N. Harpp, L. Q. Bao, C. J. Black, J. G. Gleason, and R. A. Smith, J. Org. Chem., 40, 3420 (1975)] and iodination with iodine in the presence of cupric ($Cu^{2+}$) salts [C. A. Horiuchi and J. Y. Satoh, Chem. Lett., 1509 (1984)]. The first method is impractical due to the expensive strong bases required and the latter two require a secondary oxidation to force the reaction In the case of the thionyl chloride procedure, thionyl chloride is oxidized/reduced to iodine and sulfur. In the cupric salt-induced iodinations, $Cu^{2+}$ is reduced to $Cu^{1+}$ and the copper salts must be removed by filtration.

Russian Patent 321,103 (1975) describes the reaction of iodine with ketene and the subsequent isolation of iodoacetic anhydride. This reaction presumably involves the addition of iodine to the olefinic portion of ketene.

We have discovered that α-iodocarbonyl compounds can be obtained by the reaction of molecular iodine ($I_2$) with a carboxylic acid anhydride, the carboxylic acid moiety of which contains at least one α-hydrogen atom. The reaction which occurs during our novel process is unusual in that no reoxidation of hydrogen iodide or salt formation is necessary to permit the formation of an α-iodocarbonyl. Instead, hydrogen iodide is formed and subsequently reacts with excess acetic anhydride to yield a carboxylic acid iodide.

The process provided by this invention may be carried out over a broad temperature range, e.g., from temperatures as low as −50° C. to as high as 300° C. Normally, however, the process temperatures will be in the range of about 0 to 175° C. The process may be conducted in the presence of an inert solvent or diluent such as lower carboxylic acids, trisubstituted carboxylic acids, e.g., pivalic acid, aromatic hydrocarbons and halogenated hydrocarbons, especially iodides, although a solvent normally is neither advantageous nor preferred. The process typically is carried out at ambient pressure although pressures moderately above or below atmospheric may be used.

The particular product, or mixture of products, obtained depends on the iodine-anhydride stoichiometry and the temperature at which the reaction is carried out. Thus, when the mole ratio of anhydride:$I_2$ is less than 2 and the process is carried out at mild temperatures, e.g., in the range of about 0 to 50° C., α-iodocarboxylic acid, mono-α-iodocarboxylic anhydride and carboxylic acid iodide are obtained. When the mole ratio of anhydride:$I_2$ is 2 or greater, the primary product is mono-α-iodocarboxylic anhydride along with the corresponding carboxylic acid and carboxylic acid iodide. When the process is carried out at elevated temperatures, e.g., in the range of about 60 to 200° C, or the reaction is carried out at a lower temperature and then heated at such a higher temperature, the product consists of a mixture of an α-iodocarboxylic acid and an α-iodoketone.

A preferred embodiment of our invention comprises reacting molecular iodine with a carboxylic acid anhydride, the carboxylic acid moiety of which contains at least one α-hydrogen atom, in an anhydride:$I_2$ mole ratio of greater than 2, preferably in the range of about 10:1 to 100:1, to obtain a mono-α-iodocarboxylic anhydride, e.g., an anhydride having the formula

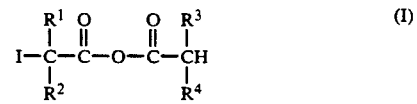

wherein $R^1$, $R^2$, $R^3$ and $R^4$ are defined below. The process may be carried out at about −50° to 300° C. although temperatures moderately above or below ambient temperature, e.g., about 15 to 30° C., are preferred. The mono-α-iodocarboxylic anhydride may be isolated, e.g., as described in the above-cited Russian patent, or, preferably, it may be converted to the corresponding α-iodocarboxylic acid by the addition of water. Alternatively, the mono-α-iodocarboxylic anhydride may be reacted with a hydroxy compound such as an alcohol to obtain a mixture of the α-iodocarboxylic acid and the ester thereof.

The carboxylic acid anhydrides which may be employed in our novel process are not critical so long as the acid moiety thereof contains at least one α-hydrogen atom. The anhydrides may contain up to 30 or more carbon atoms and may be any anhydride of the vast number of carboxylic acids which may be converted to their anhydrides according to known procedures, e.g., by reaction with acetic anhydride. Typical anhydride reactants have the formula

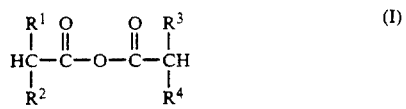
(I)

wherein $R^1$, $R^2$, $R^3$ and $R^4$ are the same or different and each is hydrogen or an unsubstituted or substituted alkyl, cycloalkyl or carbocyclic or heterocyclic aryl radical. Preferred anhydride reactants of formula (I) are those in which $R^1$ and $R^3$ each is hydrogen, alkyl of up to about 20 carbon atoms, cyclohexyl, phenyl or phenyl substituted with alkyl of up to 8 carbon atoms, alkoxy of up to 8 carbon atoms, hydroxyl or halogen and $R^2$ and $R^4$ each is hydrogen or lower alkyl, i.e., alkyl of 1 to about 4 carbon atoms.

Although not essential, the inclusion of an acid acceptor during the process to react with and consume the hydrogen iodide formed advantageously increases the selectivity of the process to form α-iodocarboxylic acids. Examples of suitable acid acceptors include salts of weak acids and strong bases such as alkali carboxylates, e.g., sodium and potassium acetate, tertiary amines such as trialkylamines, e.g., triethyl-and tributyl-amine, and pyridines including methyl-substituted pyridines. The amount of acid acceptor required to produce a beneficial effect on the process is in the range of about 0.1 to 10.0 moles of acid acceptor per mole of elemental iodine used.

The selectivity for the production of α-iodo-carboxylic acids also can be increased by performing the process under visible or ultraviolet irradiation. An ordinary tungsten flood lamp is sufficient to produce this beneficial effect.

Our novel process is further illustrated by the following examples. Several different analytical techniques were used in determining the iodine-containing components (iodoacetic acid, acetyl iodide, iodoacetone and methyl iodide) in the reaction mixtures. The iodoacetyl content was established by hydrolysis of the sample with a portion of water equivalent to 20 weight percent of the sample. The hydrolyzed sample was subsequently analyzed using ion chromatography coupled with an electrochemical detector and is reported in terms of the α-iodocarboxylic acid after correction for the quantity of water used in the hydrolysis. Acetyl iodide was also determined after hydrolysis. The level of acetyl iodide was then determined using standard analytical techniques for the determination of iodide. Iodoacetone and methyl iodide were determined by gas chromatography analysis. The "Amount" of each component is given in parts per million based on the weight of the final reaction mixture. The "Iodine Accountability" is the weight percent of the total iodine represented by each component. The iodine not accounted for was primarily unreacted molecular iodine. The "Yields" (percent of theoretical yield) reported in the examples are based on the stoichiometry in the equation:

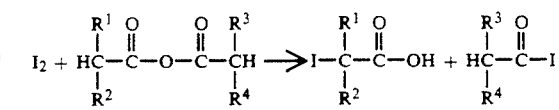

EXAMPLE 1

Molecular iodine (0.221 g) was dissolved in acetic anhydride (1 kg) and the solution was stirred for 6 hours at ambient temperature. The results of analyses of the hydrolysis mixture were:

| Component | Amount | Yield | Iodine Accountability |
|---|---|---|---|
| Iodoacetic Acid | 99 | 61 | 31 |
| Acetyl Iodide | 158 | 98 | 49 |
| Iodoacetone | 3 | — | 1 |
| Methyl Iodide | 3 | — | 1 |

When the above procedure is repeated using 0.219 g of molecular iodine and 1 kg of acetic acid rather than acetic anhydride, no iodoacetic is detected in the final reaction mixture.

EXAMPLE 2

This example demonstrates the ability to shift the selectivity to favor α-iodoketones over acyl iodides as the temperature is increased. Molecular iodine (0.163 g) was dissolved in acetic anhydride (1 kg) and the solution was heated at reflux (140° C.) for 6 hours. The results of analyses of the hydrolysis mixture were:

| Component | Amount | Yield | Iodine Accountability |
|---|---|---|---|
| Iodoacetic Acid | 86 | 72 | 36 |
| Acetyl Iodide | 104 | 87 | 44 |
| Iodoacetone | 40 | — | 17 |
| Methyl Iodide | 1.4 | — | 1 |

When the above procedure is repeated using 0.219 g of molecular iodine and 1 kg of acetic acid rather than acetic anhydride, no iodoacetic is detected in the final reaction mixture.

EXAMPLE 3

This example demonstrates that the reaction can be extended to include solutions of carboxylic anhydrides and their parent acids. Molecular iodine (0.220 g) was dissolved in a mixture of acetic anhydride (700 g) and acetic acid (300 g) and the solution was heated at reflux (140° C.) for 6 hours. The results of analyses of the hydrolysis mixture were:

| Component | Amount | Yield | Iodine Accountability |
|---|---|---|---|
| Iodoacetic Acid | 85 | 54 | 26 |
| Acetyl Iodide | 114 | 68 | 34 |
| Iodoacetone | 0.5 | — | — |

| Component | Amount | Yield | Iodine Accountability |
| --- | --- | --- | --- |
| Methyl Iodide | 4.0 | — | 2 |

EXAMPLE 4

Molecular iodine (0.1663 g) was dissolved in propanoic anhydride (1 kg) and the solution was heated at reflux (140° C.) for 6 hours. The results of analyses of the hydrolysis mixture were:

| Component | Amount | Yield | Iodine Accountability |
| --- | --- | --- | --- |
| α-Iodopropanoic Acid | 110 | 84 | 42 |
| Propanoyl Iodide | 51 | 39 | 20 |
| Ethyl Iodide | 22 | — | 11 |
| Methyl Iodide | 7.1 | — | 2 |

EXAMPLE 5

This example demonstrates the assistance of light in shifting the selectivity in favor of α-iodocarboxylic acids. Molecular iodine (0.212 g) was dissolved in acetic anhydride (1 kg) and the solution was stirred for 6 hours while it was irradiated using a 150 watt tungsten lamp. The lamp caused the temperature to rise to the point that a slow reflux was established. The results of analyses of the final mixture were:

| Component | Amount | Yield | Iodine Accountability |
| --- | --- | --- | --- |
| Iodoacetic Acid | 157 | 101 | 51 |
| Acetyl Iodide | 120 | 79 | 39 |
| Methyl Iodide | 2.3 | — | 1 |

The mixture also contained iodoacetone which was not quantified.

EXAMPLE 6

This example demonstrates the use of an acid acceptor in the process to assist in the removal of hydrogen iodide. A solution of molecular iodine (155 ppm, 0.61 millimole/kg) and sodium acetate (56 ppm, 0.68 millimole) in acetic anhydride was stirred for 6 hours at ambient temperature. The results of analyses of the hydrolysis mixture were:

| Component | Amount | Yield | Iodine Accountability |
| --- | --- | --- | --- |
| Iodoacetic Acid | 99 | 87 | 44 |
| Acetyl Iodide | 19 | — | 8 |
| Methyl Iodide | 0.2 | — | 0 |

The invention has been described in detail with particular reference to preferred embodiments thereof, but it will be understood that variations and modifications will be effected within the spirit and scope of the invention.

We claim:

1. Process for the preparation of α-iodocarbonyl compounds which comprises reacting molecular iodine with a carboxylic acid anhydride.

2. Process according to claim 1 for the preparation of α-iodocarbonyl compounds which comprises reacting molecular iodine with a carboxylic acid anhydride having the formula

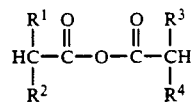

wherein $R^1$, $R^2$, $R^3$ and $R^4$ are the same or different and each is hydrogen or an unsubstituted or substituted alkyl, cycloalkyl or carbocyclic or heterocyclic aryl radical.

3. Process for the preparation of mono-α-iodo-carboxylic anhydride which comprises reacting a carboxylic anhydride, the carboxylic acid moiety of which contains at least one α-hydrogen atom, with molecular iodine at a temperature of about 0 to about 175° C., wherein the mole ratio of anhydride:$I_2$ is at least 2.

4. Process for the preparation of mono-α-iodo-carboxylic anhydride which comprises reacting a carboxylic anhydride having the formula

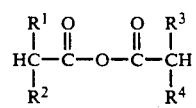

wherein $R^1$ and $R^3$ each is hydrogen, alkyl of up to about 20 carbon atoms, cyclohexyl, phenyl or phenyl substituted with alkyl of up to 8 carbon atoms, alkoxy of up to 8 carbon atoms, hydroxyl or halogen and $R^2$ and $R^4$ each is hydrogen or lower alkyl, with molecular iodine at a temperature of about 0 to 175° C., wherein the mole ratio of anhydride:$I_2$ is about 10:1 to 100:1.

5. Process according to claim 4 wherein the anhydride is acetic or propanoic anhydride.

6. Process for the preparation of mono-α-iodo-carboxylic anhydride which comprises reacting a carboxylic anhydride, the carboxylic acid moiety of which contains at least one α-hydrogen atom, with molecular iodine in the presence of an acid acceptor at a temperature of about 0° to about 175° C., wherein the mole ratio of anhydride:$I_2$ is at least 2.

7. Process according to claim 6 for the preparation of mono-α-iodocarboxylic anhydride which comprises reacting a carboxylic anhydride having the formula

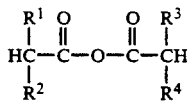 (I)

wherein $R^1$ and $R^3$ each is hydrogen, alkyl of up to about 20 carbon atoms, cyclohexyl, phenyl or phenyl substituted with alkyl of up to 8 carbon atoms, alkoxy of up to 8 carbon atoms, hydroxyl or halogen and $R^2$ and $R^4$ each is hydrogen or lower alkyl, with molecular iodine in the presence of an alkali metal carboxylate at a temperature of about 0° to 175° C., wherein the mole ratio of anhydride:$I_2$ is about 10:1 to 100:1 and the mole ratio of the alkali metal carboxylate:$I_2$ is about 0.1 to 10.0.

8. Process according to claim 7 wherein the anhydride is acetic or propanoic anhydride and the acid acceptor is sodium or potassium acetate.

9. Process for the preparation of a mixture of a mono-α-iodocarboxylic anhydride and an α-iodoketone which comprises reacting a carboxylic anhydride, the carboxylic acid moiety of which contains at least one α-hydrogen atom, with molecular iodine at a temperature of about 60° to about 175° C., wherein the mole ratio of anhydride:I$_2$ is at least 2.

10. Process for the preparation of a mixture of a mono-α-iodocarboxylic anhydride and an α-iodoketone which comprises reacting a carboxylic anhydride having the formula

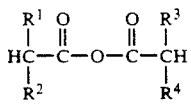

wherein R$^1$ and R$^3$ each is hydrogen, alkyl of up to about 20 carbon atoms, cyclohexyl, phenyl or phenyl substituted with alkyl of up to 8 carbon atoms, alkoxy of up to 8 carbon atoms, hydroxyl or halogen and R$^2$ and R$^4$ each is hydrogen or lower alkyl, with molecular iodine at a temperature of about 60° to 175° C., wherein the mole ratio of anhydride:I$_2$ is about 10:1 to 100:1.

* * * * *